United States Patent [19]

McDermott et al.

[11] Patent Number: 5,571,531
[45] Date of Patent: Nov. 5, 1996

[54] MICROPARTICLE DELIVERY SYSTEM WITH A FUNCTIONALIZED SILICONE BONDED TO THE MATRIX

[75] Inventors: Mark R. McDermott; Michael A. Brook, both of Ancaster; Philippa L. Heritage, Hamilton; Brian J. Underdown, Dundas; Lesley M. Loomes; Jianxiong Jiang, both of Hamilton, all of Canada

[73] Assignee: McMaster University, Hamilton, Canada

[21] Appl. No.: 245,646

[22] Filed: May 18, 1994

[51] Int. Cl.$^6$ .............................. A61K 9/56; A61K 9/50; A61K 9/14; A01N 25/34
[52] U.S. Cl. .................. 424/459; 424/408; 424/488; 424/499; 424/184.1; 424/209.1; 424/231.1
[58] Field of Search ........................... 424/231.1, 209.1, 424/184.1, 499, 408, 459, 488

[56] References Cited

U.S. PATENT DOCUMENTS

| | | |
|---|---|---|
| 4,251,387 | 2/1981 | Lim . |
| 4,389,330 | 6/1983 | Tice . |
| 4,798,786 | 1/1989 | Tice . |
| 4,970,156 | 11/1990 | Avrameas . |
| 5,075,109 | 12/1991 | Tice ........................................... 424/88 |
| 5,104,566 | 4/1992 | Guerin . |
| 5,151,264 | 9/1992 | Samain ..................................... 424/1.1 |
| 5,407,682 | 4/1995 | Schacht et al. . |

FOREIGN PATENT DOCUMENTS

| | | |
|---|---|---|
| WO91/06282 | 5/1991 | WIPO . |
| 9109678 | 7/1995 | WIPO . |

OTHER PUBLICATIONS

Saito, N. et al Yakuzaigaku (1991) 51(2), pp. 73–79 Abstract Only O/W Emulsion of Dimethyl Poly Siloxane for Oral Use Prepared w/Nonionic Surfactants.

Moldoveanu et al. J. Inf. Dis 1993 vol. 167 pp. 84–90 Oral Immunization With Influenza Virus in Biodegradable Microspheres.

Eldridge, J. H. et al. (1991) Adv. Exp. Med. Biol. pp. 340–345 Vaccine-Containing Biodegrable Microspheres Spec. Enter the Gut. Assoc. Lymphoid Tissue Following Oral Admin. & Induce . . . .

Morris W. et al Vaccine (1994) pp. 5–10 Potential of Polymer Microencapsulation.

Primary Examiner—James C. Housel
Assistant Examiner—Jennifer Shaver
Attorney, Agent, or Firm—Sim & McBurney

[57] ABSTRACT

A particulate carrier for an agent comprising a solid core of a polysaccharide and a proteinaceous material and an organometallic polymer bonded to the core is provided. The agent has a biological activity, such as immunogenicity, and may comprise the proteinaceous material or be a separate component of the core. Polysaccharide cores include dextran, starch, cellulose and derivatives thereof and the organometallic polymer includes silicones including substituted silicones. The particulate carriers are useful for delivering agents to the immune system of a subject by mucosal or parenteral administration to produce immune responses, including antibody responses.

30 Claims, 12 Drawing Sheets

```
                    ┌─────────────────────────┐
                    │  starch dissolved in DMSO │
                    │   85 °C, 5min., stirring  │
                    └─────────────────────────┘
                              │ cool to < 37°C
                              ▼
   ┌─────────┐      ┌──────────────────┐      ┌──────────────────┐
   │   HSA   │      │ HSV-2 lysate/HSA │      │  Flu X31 / HSA   │
   └─────────┘      └──────────────────┘      └──────────────────┘
            ↘              │                  ↙
                  stir to form highly
                   viscous mixture
                           │
                  add dropwise to vegetable oil
                           │           ◀─ ─ ─ ─ ─ add surfactant
                   stir vigorously
                           ▼
                  ┌──────────────────┐
                  │   water-in-oil   │
                  │     emulsion     │
                  └──────────────────┘
                           │ sonicate
                           ▼
                  add dropwise with stirring
                       ↙          ↘
   ┌───────────────────────────┐   ┌───────────────────────────┐
   │ acetone + 0.125% Tween 80 │   │ acetone + 0.125% TS-PDMS  │
   └───────────────────────────┘   └───────────────────────────┘
                │                                 │
                ▼                                 ▼
   ┌───────────────────────────┐   ┌───────────────────────────┐
   │    uncoated starch        │   │   TS-PDMS-coated starch   │
   │     microparticles        │   │      microparticles       │
   └───────────────────────────┘   └───────────────────────────┘
                      ↘                     ↙
                      harvest by centrifugation
                               │
                               ▼
                       dry by exposure to air
```

FIG.1.

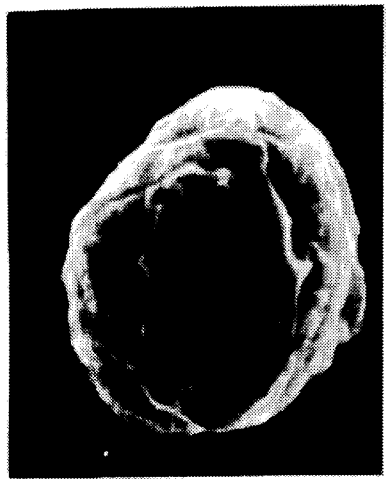
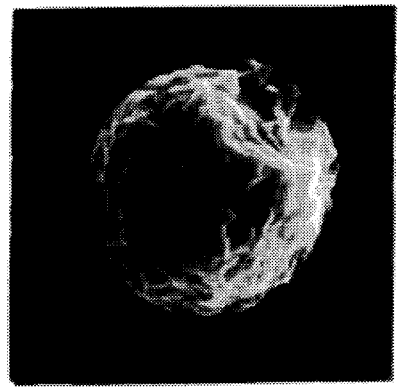
FIG. 2A.
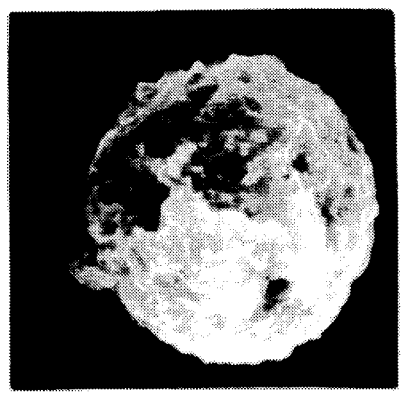
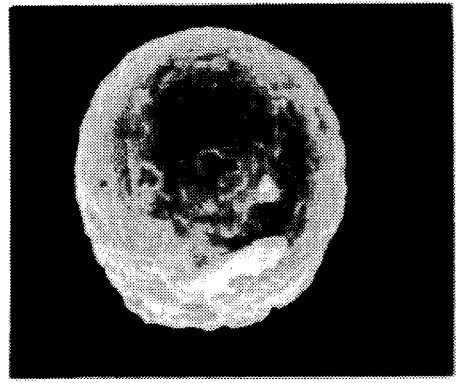
FIG. 2B.

MICROPARTICLE DELIVERY SYSTEM WITH A FUNCTIONALIZED SILICONE BONDED TO THE MATRIX

FIELD OF INVENTION

The present invention relates to a particulate carrier for delivering materials having biological activity. The term "microparticle" as used herein refers to any particulate carrier used for delivery of a biologically-active material and includes materials which are microcapsules and microspheres.

BACKGROUND OF THE INVENTION

Vaccines have been used for many years to protect humans and animals against a wide variety of infectious diseases. Such conventional vaccines consist of attenuated pathogens (for example, polio virus), killed pathogens (for example, *Bordetella pertussis*) or immunogenic components of the pathogen (for example, diphtheria toxoid). Some antigens are highly immunogenic and are capable alone of eliciting protective immune responses. Other antigens, however, fail to induce a protective immune response or induce only a weak immune response. This low immunogenicity can be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate are routinely used as adjuvants in human and veterinary vaccines. However, even these adjuvants are not suitable for use with all antigens and can also cause irritation at the site of injection. There is a clear need to develop novel adjuvants which are safe and efficacious for enhancing the immunogenicity of antigens.

Immunization can also be achieved by the delivery of antigens to mucosal surfaces, such as by ingestion of the antigen. Thus, it is known that the ingestion of antigens by animals can result in the appearance of antigen-specific secretory IgA antibodies in intestinal, bronchial or nasal washings and other external secretions. For example, studies with human volunteers have shown that oral administration of influenza vaccine is effective at inducing secretory anti-influenza antibodies in nasal secretions and substances have been identified which might be useful as adjuvants for such ingested vaccines. However, most of these adjuvants are relatively poor in terms of improving immune responses to ingested antigens. Currently, some of these adjuvants have been determined to be safe and efficacious in enhancing immune responses in humans and animals to antigens that are administered via the orogastrointestinal, nasopharyngeal-respiratory and genital tracts or in the ocular orbits. However, administration of antigens via these routes is generally ineffective in eliciting an immune response. The inability to immunize at the mucosal surface is generally believed to be due to:

the destruction of the antigen or a reduction in its immunogenicity in the acidic and/or enzymatically hostile environments created by secretions produced at the mucosal epithelium;

the dilution of the antigen to a concentration that is below that required to induce immune responses;

the carriage of antigen from the body in discharges originating at the mucosal epithelium; and the lack of suitable adjuvants which remain active at the mucosal epithelium.

Clearly, there is a need to identify powerful adjuvants which are safe and efficacious for use at the mucosal epithelium in the orogastrointestinal, nasopharyngeal-respiratory and urogenital tracts and in the ocular orbits and at other mucosal sites.

Sensitive antigens may be entrapped to protect them against destruction, reduction in immunogenicity or dilution. The antigen can be coated with a single wall of polymeric material or can be dispersed within a monolithic matrix. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof. However, U.S. Pat. No. 5,151,264 does not describe particulate carriers containing antigens for immunization and particularly does not describe particulate carriers for immunization via the orogastrointestinal, nasopharyngeal-respiratory and urogenital tracts and in the ocular orbits or other mucosal sites.

U.S. Pat. No. 5,075,109 describes encapsulation of the antigens trinitrophenylated keyhole limpet hemocyanin and staphylococcal enterotoxin B in 50:50 poly (DL-lactide-co-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly(8-hydroxybutyric acid), and polyanhydrides. The encapsulated antigen was administered to mice via gastric intubation and resulted in the appearance of significant antigen-specific IgA antibodies in saliva and gut secretions and in sera. As stated in this patent, in contrast, the oral administration of the same amount of unencapsulated antigen was ineffective at inducing specific antibodies of any isotype in any of the fluids tested. Poly(DL-lactide-co-glycolide) microcapsules were also used to administer antigen by parenteral injection.

Published PCT application WO 91/06282 describes a delivery vehicle comprising a plurality of bioadhesive microspheres and antigenic vaccine ingredients. The microspheres being of starch, gelatin, dextran, collagen or albumin. This delivery vehicle is particularly intended for the uptake of vaccine across the nasal mucosa. The delivery vehicle may additionally contain an absorption enhancer. The antigens are typically encapsulated within protective polymeric materials.

SUMMARY OF THE INVENTION

The present invention is directed towards the provision of a new and useful microparticle delivery system, which may be used for delivery of materials having biological activity, including antigens to a host.

In accordance with one aspect of the present invention, there is provided a particulate carrier, which comprises:

a solid core comprising a polysaccharide and a proteinaceous material; and an organometallic polymer bonded to the core. Such particulate carrier generally has a particle size from about 10 nm to about 50 μm, preferably from about 1 to about 10 μm.

The polysaccharide component of the core may be dextran, starch, cellulose or derivatives thereof, particularly soluble starch. The starch may be derived from a variety of monocotyledenous and dicotyledenous species, such as corn, potato or tapioca.

The proteinaceous material component of the core may have biological activity. An additional material having biological activity also may be included in the core. The particles then provide a delivery vehicle for the biologically-active material to a host, generally an animal, including a human.

The material having biological activity, for example, immunogenicity, includes proteins (such as influenza viral protein), peptides, antigens, bacteria, bacterial lysates, viruses (such as, influenza virus), virus-infected cell lysates (such as, a herpes simplex virus-infected cell lysate), antibodies, carbohydrates, nucleic acids, lipids, haptens, pharmacologically-active materials, and combinations, derivations and mixtures thereof.

The organometallic polymer bonded to the core preferably is derived from a functionalized silicone, including an end-substituted silicone. One particular class of end-substituted silicones from which the organometallic polymer may be derived are (trialkoxysilyl) alkyl-terminated polydialkxylsiloxanes.

In a further aspect of the present invention, there is provided an immunogenic composition formulated for mucosal or parenteral administration, comprising the particulate carrier containing an immunogenic material and a physiologically-acceptable carrier therefor.

In an additional aspect, there is provided a method of producing an immune response in a host, comprising the administration thereto, generally by mucosal or parenteral administration, the immunogenic composition provided herein. The immune response produced may be an antibody response, including local and serum antibody responses.

In a further aspect of the present invention, there is provided a method for producing a particulate carrier, which comprises:

(a) forming an aqueous composition comprising a dissolved polysaccharide and a dispersed or dissolved proteinaceous material;

(b) forming an emulsion in which the aqueous composition is the dispersed phase;

(c) forming from the emulsion a particulate carrier comprising a core of said polysaccharide and proteinaceous material having bonded thereto an organometallic polymer; and (d) collecting the particulate carrier so formed.

The method may optionally include a step of sonicating the suspension of microspheres to produce a fine suspension before the forming step (c), so as to control particle size.

This procedure enables the proteinaceous material to be incorporated into the microparticles under temperature conditions which do not denature the proteinaceous material or adversely affect the biological activity thereof.

Advantages of the present invention include:

(a) ease and safety of microparticle manufacture;

(b) biocompatability and safety of the microparticles;

(c) improved immunogenicity of antigens presented to cells of the immune system by the microparticles;

(d) ease of storage and administration; and (e) fabrication conditions that do not adversely affect the biological activity of proteinaceous or other material.

In this application, the term "coated" microparticles is used to define microparticles that have a long chain organometallic polymer bound, bonded or otherwise associated with the core thereof.

BRIEF DESCRIPTION OF THE DRAWINGS

FIG. 1 shows a flow diagram for a process for the production of starch microparticles according to one embodiment of the invention. In this Figure, HSA=human serum albumin, HSV2-lysate/HSA=herpes simplex virus type-2 lysate mixed with human serum albumin, Flu X31/HSA =influenza virus strain X31 mixed with human serum albumin.

FIG. 2 shows scanning electron microscopy (SEM) analysis of influenza virus strain A-X31 and human serum albumin—containing microparticles that were either (A) coated with the silicone polymer s(triethoxysilyl)propyl-terminated polydimethysiloxane (TS-PDMS) or (B) were uncoated. The SEM images represent magnification of 2500 diameters. The nominal diameter of the TD-PDMS-coated microparticles was 10 μm and that of uncoated microparticles was 10 μm.

GENERAL DESCRIPTION OF THE INVENTION

Figure 3:
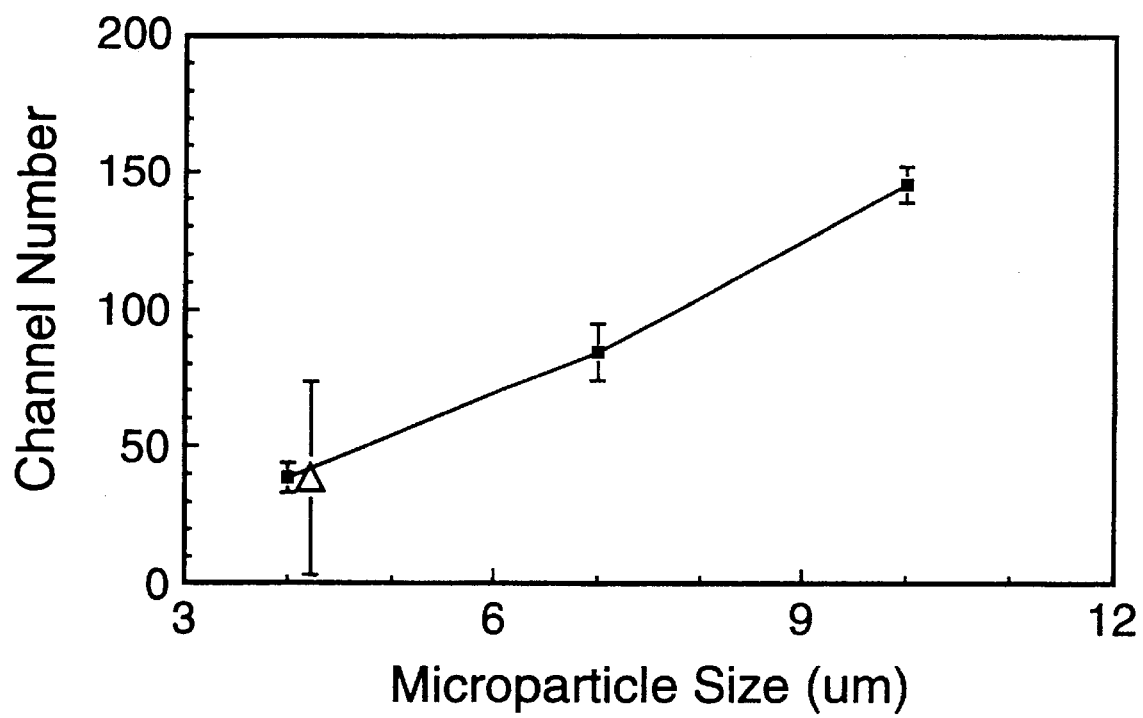
FIG. 3 shows the diameter distribution of human serum albumin-containing starch microparticles coated with the silicone polymer 3-(triethoxyl) silylpropyl-terminated polydimethylsiloxane (TS-PDMS). HSA-containing starch particles (Δ) were fabricated and compared to polystyrene microsphere standards by flow cytometry ( -■-; 10 μm, 7 μm, 4 μm diameter). The particles had a mean diameter of 4.18 μm and a standard deviation of plus or minus 3 μm.

As noted above, the present invention relates to a particulate carrier or microparticle, which is useful for the delivery of biologically-active materials to a vertebrate, generally an animal including humans, including the delivery of antigens to the immune system, by mucosal or parenteral administration.

The particulate carrier comprises two components, namely a solid core and an organometallic polymer bonded to the core.

The solid core comprises at least two components, namely a polysaccharide and a proteinaceous material. The polysaccharide may be one of a wide range of such materials, preferably starch, particularly starch which has been treated as to be "soluble" starch (i.e. a starch which has been treated to provide a starch which is soluble in water). However, other polysaccharide materials may be used, including dextran and cellulose, as well as derivatives and mixtures of two or more polysaccharides.

The particulate carrier may have a particle size which generally ranges from about 10 nm to about 50 μm and preferably about 1 to about 10 μm for mucosal administration of antigens.

The proteinaceous material may be any desired proteinaceous material and may itself have biological activity. Examples of proteinaceous materials which may be used are proteins derived from a variety of viruses and bacteria including tetanus toxoid, diphtheria toxoid, cholera toxoid and subunits thereof, pertussis toxoid, viral subunits, such as rubella virus proteins E1, E2 and C, bacterial subunits, such as the P41, OspA and OspB proteins of *B. burgdorferi*, protein-polysaccharide conjugates, protozoan subunits, such as *T. gondi* P30, anticoagulants, venoms, such as snake venom, cytokines, such as interleukins 4, 5, 6 and 12, interferons, tumour necrosis factor, and albumins, such as human serum albumin, bovine serum albumin and ovalbumin, as well as recombinant proteins, peptides and lipopeptides and analogs thereto, including muramyl dipeptide, lipopolysaccharide and lipid A or analogues of such proteins or of immunologic regions of such proteins.

Where the proteinaceous material has biological activity, an additional biologically-active material may or may not be included in the core. Where the proteinaceous material lacks biological activity, a material having biological activity may be incorporated into the core, so that the proteinaceous material acts as a carrier for the biologically-active material.

Both the polysaccharide and proteinaceous material are required to be present for microparticle formation and organometallic polymer coating. In the absence of one of the components, it has not been possible to obtain the particulate carrier of the invention. The proportion of the core comprising proteinaceous material may vary up to about 33 wt % of the core, generally from about 0.5 wt % to about 10 wt %.

Where a biologically-active material is present in the core other than in the form of the proteinaceous material, such material may comprise from about 0.5 to about 30 wt % of the core, preferably from about 0.5 to about 5.0 wt %. Such biologically-active material may be any member of the various classes of known biologically-active materials, including proteins, peptides, antigens, antibodies, immunotargeting molecules, bacteria, bacterial lysates, viruses, virus-infected cell lysates, antibodies, carbohydrates, nucleic acids, lipids, glycolipids, haptens, pharmacologically-active materials, as well as combinations, derivatives and mixtures thereof. Specific examples of such materials include influenza viruses, parainfluenza viruses, respiratory viruses, measles viruses, mumps viruses, human immunodeficiency viruses, polio viruses, rubella viruses, herpex simplex viruses type 1 and 2, hepatitis viruses types A, B and C, yellow fever viruses, smallpox viruses, rabies viruses, vaccinia viruses, reo viruses, rhinoviruses, Coxsackie viruses, Echoviruses, rotaviruses, papilloma viruses, paravoviruses and adenoviruses; *E. coli*, *V. cholera*, BCG, *C. diphtheria*, *Y. pestis*, *S. typhi*, *B. pertussis*, *S. aureus*, *S. pneumoniae*, *S. pyogenes*, *S. mutans*, Myocoplasmas, Yeasts, *C. tetani*, meningococci (*N. meningitdis*), Shigella spp, Campylobacter spp, Proteus spp, *Neisseria gonorrhoeae*, and *Haemophilus influenzae*; as well as proteins obtained from such viruses and bacteria.

The solid core has an organometallic polymer bonded thereto. Such organometallic compounds may include linear, branched or cross-linked silicones which are bonded at the ends of polymer chains to the core, although the polymer may be bonded to the core at locations along the length of the chain. Such polysiloxanes may vary in molecular weight from about 400 up to about 1,000,000 Daltons and preferably from about 700 to about 60,000 Daltons.

A variety of polysiloxanes may be employed. For the purpose of bonding the polysiloxane to the solid core, the polysiloxanes preferably are derived from functionalized materials which have functional groups at the ends of the polymer chain which facilitate bonding the ends of the polysiloxane chain to the solid core. Preferably, however, where such functional groups are present, they are joined to the polysiloxane chain through end-blocking groups.

Suitable functionalized silicones useful for forming the products of the invention include (trialkoxysilyl) alkyl-terminated polydialkylsiloxanes and trialkoxysilylterminated polydialkylsiloxanes. One useful member of this group of compounds is 3-(triethoxysilyl) propyl-terminated polydimethylsiloxane (herein abbreviated as TS-PDMS).

The organometallic polymer is present in the particulate carrier in relatively minor amounts, generally from about 0.5 to about 5 wt % of the solid core. The presence of the organometallic polymer, particularly a silicone, bonded to the solid core enables biologically-active materials to be administered to a host, particularly by mucosal administration, to achieve an enhanced biological response to such material, for example, an enhanced immune response to an antigen, in comparison to delivery of the material by the same particulate material without the organometallic polymer bonded thereto, as seen from the data presented herein.

The particulate carrier provided herein may be formed in any convenient manner permitting coated particle formation. One preferred procedure is described below with reference to FIG. 1.

DESCRIPTION OF THE PREFERRED EMBODIMENT

Referring to FIG. 1, there is shown a method for preparing starch microparticles according to one embodiment of the present invention. Antigen-containing starch microparticles are manufactured by mixing starch and the antigen in solvents, forming an emulsion in oil, and then dispersing the emulsion into an acetone solution with vigorous stirring and collecting the particles formed. The starch or other polysaccharide first is dissolved in a solvent suitable for the polysaccharide. For starch, dimethylsulfoxide is a preferred solvent, in which starch, for example, "soluble" starch, is dissolved at a elevated temperature, for example, a temperature of about 50° to about 100° C., preferably about 75° to about 90° C. and then cooled to a lower temperature, particularly to a temperature below about 35° C., without precipitating therefrom. Alternative polar solvents which may be used as solvents for the starch, including dimethylformamide as well as various alcohols.

The starch solution is mixed with an aqueous solution and/or dispersion of a proteinaceous material, in the illustrated embodiment, human serum albumin (HSA), which may be used alone as an antigen or combined with other antigenic material, for example, a herpes simplex virus type 2 (HSV-2) infected cell lysate or a whole influenza virus (Flu X31), in which event the HSA acts also as a carrier protein.

Mixing of the starch solution and antigen composition generally produces by stirring, a highly viscous mixture, which then is added dropwise into vegetable oil, or other water-immiscible fluid which is capable of forming a water-in-oil emulsion, including silicone oils or derivatives thereof or mixtures thereof, with vigorous stirring to promote the formation of a water-in-oil emulsion, in which droplets of the starch-proteinaceous material composition are dispersed in the vegetable oil. This step of the process, therefore, involves forming an emulsion in which the aqueous composition is the dispersed phase.

The particle size of the liquid droplets, which determines the size of the ultimate carrier microparticles, is determined by the volumetric ratio of aqueous phase to oil phase, by the degree of stirring of the water-in-oil emulsion and may further be controlled by sonication. Additional control of particle size may be achieved by employing a surfactant in the oil, such as non-ionic surfactants of the TWEEN or SPAN type.

The water-in-oil emulsion then may be added dropwise to a solvent for the oil and aqueous medium containing the starch, proteinaceous material and antigen, to result in microparticle formation. In the procedure of the present invention, the solvent also contains a silicone polymer material which can bond to the solid core produced by the solvent. Alternatively, some or all the silicone oil can be included in the vegetable oil or silicone oil can replace all or part of the vegetable oil. (FIG. 1 also illustrates an alternative procedure, employed in the Examples below to produce particulate carrier lacking the silicone polymer, for comparative experimentation.)

The solvent which may be employed for such dessication and oil dissolution may be any organic solvent miscible with the oil and water phases of the emulsion and in which the starch and proteinaceous material are substantially insoluble. Such solvents include but are not limited to ketones, such as acetone and methyl ethyl ketone.

The silicone polymer dissolved in the solvent may be a functionalized polysiloxane, particularly end-functionalized, to permit bonding of the polysiloxane to the solid core of the particulate material. Such functionalized polysiloxane may include 3-(trialkoxysilyl) alkyl-terminated polydialkylsiloxanes, particularly 3-triethoxysilyl) propyl-terminated polydimethylpolysiloxane (TS-PDMS).

The resulting particulate material may be harvested from the residual medium by any convenient means, including centrifugation, separated and dried. The particulate material resulting from this procedure then is in a suitable form for formulation for administration of the biologically-active material.

It is clearly apparent to one skilled in the art, that the various embodiments of the present invention have many applications in the fields of medicine and in particular vaccination, diagnosis and treatment of infections with pathogens including bacteria and viruses. A further non-limiting discussion of such uses is further presented below.

Vaccine Preparation and Use

In an embodiment, immunogenic compositions, suitable to be used as, for example, vaccines, may be prepared from microparticles as disclosed herein. The immunogenic composition elicits an immune response by the host to which it is administered including the production of antibodies by the host.

The immunogenic composition may be prepared as injectables, as liquid solutions or emulsions. The microparticles may be mixed with physiologically acceptable carriers which are compatible with the microparticles. These may include, water, saline, dextrose, glycerol, ethanol and combinations thereof. The vaccine may further contain auxiliary substances such as wetting or emulsifying agents, pH buffering agents, or adjuvants to further enhance the effectiveness of the vaccines. Vaccines may be administered by injection subcutaneously or intramuscularly.

Alternatively, and in a preferred embodiment, the immunogenic compositions comprising microparticles formed according to the present invention, may be delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the microparticles of the present invention. In order to protect the microparticles and the material having biological activity contained within the core of the microparticle, from gastric acidity when administered by the oral route, an acidic neutralizing preparation (such as a sodium bicarbonate preparation) is advantageously administered before, concomitant with or directly after administration.

The vaccines are administered in a manner compatible with the dosage formulation, and in such amount as to be therapeutically effective, protective and immunogenic. The quantity to be administered depends on the subject to be treated, including, for example, the capacity of the subject's immune system to synthesize antibodies, and if needed, to produce a cell-mediated immune response. Precise amounts of microparticle and material having biological activity required to be administered depend on the judgement of the practitioner. However, suitable dosage ranges are readily determinable by one skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the production of antigen-containing starch microparticles.

A flow diagram summarising the process of starch microparticle production effected herein is shown in FIG. 1. Antigen-containing starch microparticles were manufactured by mixing starch and the antigen in solvents, forming an emulsion in oil, and then dispersing the emulsion into an acetone solution with vigorous stirring and collecting the particles formed. Starch microparticles were separately manufactured containing the antigens, human serum albumin (HSA), herpes simplex virus type 2 (HSV-2)—infected cell lysate and whole influenza virus. To form the HSV-2 and influenza virus-containing starch microparticles, HSA was included as a "filler" protein.

Specifically, 1 g of soluble potato starch was added to 2 mL of dimethylsulfoxide (DMSO) while stirring the mixture. The starch was dissolved by heating the mixture to 85° C. for 5 minutes. The following amounts (Table 1) of antigen were prepared to form the antigen-containing microparticles indicated:

TABLE 1

| Antigen entrapped in starch microparticles | Antigen Preparation |
|---|---|
| HSA | 0.1 g of HSA dissolved in 1.0 mL water at room temperature. |
| HSV-2-infected cell-lysate/HSA | 25 mg of HSV-2 in 0.5 mL of buffer and 75 mg HSA in 0.5 mL $H_2O$. |
| Influenza/HSA | 25 mg Flu X31 in 1 mL 0.1M Tris, 5 mM EDTA pH 7.5, 75 mg HSA in 0.375 mL $H_2O$. |

When the starch solution had cooled to a temperature of less than 37° C., the antigen preparation indicated above was added to the cooled solution and the mixture stirred (500 rpm) at room temperature for 20 minutes to form a highly viscous mixture. This viscous mixture was added dropwise to 30.0 mL of vegetable oil and stirred vigorously (1500 rpm) for 15 minutes at room temperature to produce a water-in-oil emulsion. This water-in-oil emulsion was sonicated on ice for 60 seconds with stirring. The emulsion was then added dropwise with stirring (1000 rpm) to 400 mL of acetone containing 0,125% v/v Tween 80. The resultant particles, of approximately 4.18±3 μ were collected by centrifugation, (200 xg, 5 minutes), washed twice with acetone and dried by exposure to air at room temperature for 48 hours.

Example 2

This Example describes the coating of antigen-containing starch microparticles.

The microparticles formed in Example 1 may be coated with a variety of silicones via bonded interactions at the surface including polydimethylsiloxanes (PDMS) with different molecular weights and varied end blocks. A convenient end-functionalized silicone was 3-(triethoxysilyl)propyl-terminated polydimethylsiloxane (abbreviated to TS-PDMS).

The TS-PDMS was synthesised by the hydrosilylative addition of hydrogen-terminated PDMS to allyltriethoxysilane under the catalysis of $H_2PtCl_6$ as follows. To a mixture of 17.0 mL hydrogen-terminated PDMS (Hüls, $PDMS^H$, viscosity 1,000 cs) and 0.8 mL allyltriethoxysilane (Aldrich) (molar ratio of the functional groups $PDMS^H$: $H_2C{=}CH$ 1:3) was added 0.05 mL of a 0.1M hydrogen hexachloroplatinate(IV) hydrate solution ($H_2PtCl_6$) in i-propanol (Caledon) with stirring under the protection of nitrogen at 0° C. The solution was allowed to return to room temperature overnight. The i-propanol and unreacted allyltriethoxysilane were evaporated under reduced pressure and elevated temperature up to 140° C. for 6 hours until gas ceased to bubble from the viscous fluid. The residue was subjected to further washing with distilled water four times to remove any impurities. The product was characterized by $^1H$ NMR, $^{29}Si$ NMR, GPC and IR. The reaction involved is illustrated by the following equation:

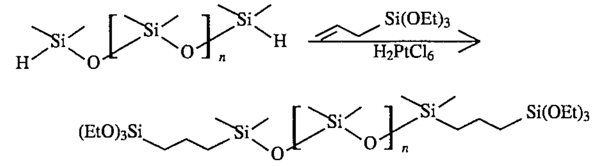

where n is the number of siloxane groups. The use of an end-functionalized silicone resulted in the formation of chemical bonds to the starch surface.

To produce particles coated with TS-PDMS and having antigens entrapped within them, the sonicated water-in-oil emulsion produced by the procedure described above in Example 1 was added dropwise with stirring (1000 rpm) to 400 mL of acetone containing 0.125% v/v TS-PDMS (1,000 c.s.) in place of the Tween 80. The resulting coated particles were harvested and dried as described in Example 1.

Example 3

This Example describes an analysis of the antigen-containing starch microparticles.

Size distributions of the antigen-containing starch microparticles prepared as described in Examples 1 and 2 were obtained by scanning electron microscopy and flow cytometry using polystyrene microparticle standards. FIG. 2 shows a scanning electron microscope analysis of HSA-containing microparticles that were either coated with TS-PDMS or were uncoated. The microparticles ranged in size from 1 to 100 μM and had a mean diameter of 4 to 5 μM as determined by flow cytometry (FIG. 3). The efficiency of antigen incorporation into starch microparticles was between 70 and 90%.

The antigen content of HSA-loaded microparticles (termed herein "core loading") was determined by incorporating an $^{125}$I-HSA tracer of known specific activity in the antigen preparation prior to microparticle formation. Protein core loading of HSA in starch microparticles was found to be about 5 to 6% by weight. This method of determining the "core-loading" could not be applied to whole influenza virus entrapped in microparticles because radiolabelled virus was found to be unstable. "Core-loading" of microparticles containing whole influenza virus was thus estimated by the release of virus by degradation of the microparticles by acid hydrolysis with HCl or enzymatic hydrolysis with human saliva.

Enzymatic hydrolysis of microparticles with human saliva was originally the preferred method as it was not anticipated to appreciably alter the antigenic integrity of the viral proteins. Microparticles were digested with 250 μL of centrifugally clarified saliva overnight at 37° C. Suspensions were centrifuged at 5000 xg for 10 minutes and the supernatants diluted 1:10 with Tris Base buffered saline (TBS, pH 7.2) containing 0.1% NaN$_3$ and stored at 4° C. until analyzed by SDS-PAGE.

"Core-loading" was determined by acid-hydrolysis of the microparticles. Thus, microparticles were incubated in 0.1M HCl for 24 hours at 37° C. Supernatants were clarified by centrifugation at 3000 rpm and filtered through a 0.45 μ filter. The solution was neutralized with 1M NaOH. Protein released from acid hydrolysed microparticles were detected using an ELISA.

The Flu X31/HSA microparticles were estimated to contain about 0.3 to 0.5% of Flu X31 and about 5 to 6% of HSA (w/w). Although HSA may be incorporated into the microparticles preferentially to Flu X31, attempts to fabricate coated microparticles without protein were unsuccessful.

Example 4

This Example describes the effects upon antigens of their entrapment in starch microparticles.

Figure 4:
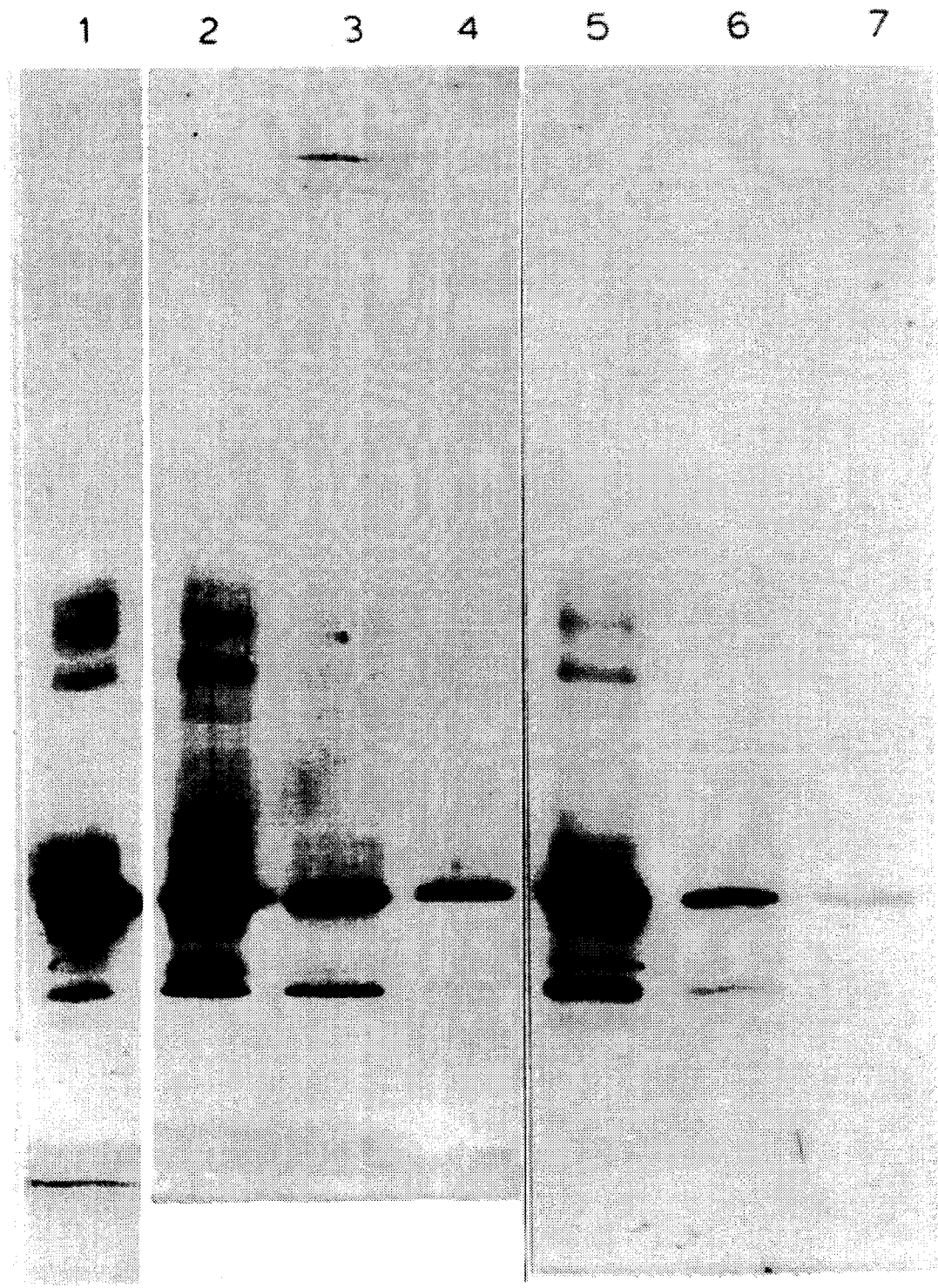
FIG. 4 shows an immunoblot analysis of human serum albumin released from human serum albumin-containing starch microparticles that were either coated with the silicone polymer 3-(triethoxysilyl)propyl-terminated polymethylsiloxane (TS-PDMS) or uncoated following suspension of the microparticles in phosphate buffered saline (PBS). Lane 1 shows 0.5 μg of an HSA standard. Lanes 2 to 4 show HSA released from TS-PDMS coated microparticles incubated for 30 min. 1h and 3h in PBS in vitro and lanes 5 to 7 show HSA released from uncoated microparticles at 30 min., 1h and 3h in vitro.

The time course samples from the antigen release studies described for HSA containing microparticles described in Example 3 were also analyzed by Western (immunoblot) analysis using an HSA-specific polyclonal antiserum. For immunodetection analysis of released HSA, the gel was equilibrated in transfer buffer (0.2M glycine, 15% methanol, 0.025M Tris Base, pH 8.3) for 15 minutes along with nitrocellulose (NC) membranes and filter paper, both of which were cut to the same size as the gel. The immunoblot apparatus was then placed in the transblot device and electrophoretic transfer was performed overnight at 30 volts. After transfer, the NC membrane was incubated with agitation in 100 mL of blocking buffer (5% w/v skim milk powder in PBS) for 2 hours. The NC membrane was then incubated with 100 mL of a 1:500 dilution of alkaline phosphatase-conjugated goat anti-HSA in blocking buffer for 2 hours at room temperature, on a tilting platform. The NC membrane was washed 3 times (10 minutes each) with PBS, and proteins were visualized by incubating the membrane with 30 mL of developing buffer (100 mM Tris Base, 100 mM NaCl, 5 mM MgCl$_2$, pH 9.5) containing 200 μL of 50 mg/mL nitroblue tetrazolium and 100 μL of 50 mg/mL 5-bromo-4-chloro-3indolylphosphate for 60 minutes. The membrane was rinsed 3 times with H$_2$O and air dried. The results of the immunoblot analysis are shown in FIG. 4. This analysis showed that HSA released into the supernatants by HCl treatment or incubation of the microparticles in PBS was detectable by an HSA-specific polyclonal antiserum. The released HSA from uncoated and TS-PDMS coated microparticles, was not fragmented by the fabrication process and was not altered in such a way as to preclude its detection by HSA-specific antibodies.

Example 5

This Example describes the immunogenicity of HSA entrapped in microparticles in mice immunised intraperitoneally.

To examine the immunogenicity of HSA entrapped in starch microparticles formed in accordance with the present invention, groups of six, 6 to 8 week old female BALB/c mice (Charles River Breeding Laboratories, Wilmington, Mass.) were immunized intraperitoneally (IP) with the following amounts of antigen in 250 μL of PBS (pH 7.4) on days 0, 7 and 14: 2 mg of TS-PDMS coated microparticles prepared as described in Examples 1 and 2 containing 100 μg of HSA; and 2 mg of uncoated microparticles containing 100 μg of HSA.

The mice showed no gross pathologies or behavioural changes after receiving either uncoated or TS-PDMS coated microparticles. Sera were obtained on days +21, +35, 49, +63 and +84 and were evaluated for the presence of anti-HSA IgG antibodies by antigen specific ELISA. All samples were analyzed in duplicate. Microtiter plate wells were incubated overnight at 4° C. with 100 μL of 10 μg/mL HSA in TBS. The plates were washed with Tris-T buffer (0.05% Tween 20 in 0.02M Tris Base, pH 7.4, containing 0.15M NaCl and 0.005M KCl). Wells were incubated with 200 μL of 0.1% gelatin in 0.02M Tris-buffered saline (TBS), pH 7.4 (operationally defined as blocking buffer). After washing with Tris-T, the plates were incubated for 2 h at 37° C. with 100 μL of sample serially diluted in blocking buffer. Wells were washed with Tris-T and 100 μL of alkaline phosphatase-conjugated goat anti-mouse IgG in blocking buffer, were added to each well. After 2 hours incubation at 37° C., the wells were washed with Tris-T and 100 μL of 1.0M diethanolamine buffer, pH 9.8, containing 0.05M MgCl$_2$ and 1.0 mg/mL of p-nitrophenylphosphate were added to each well. After 30 minutes incubation at room temperature, the optical density of the fluid in each well was determined at 405 nm using a microplate reader. A normal mouse sera pool was used to establish baseline optical density values in the assay. Hyperimmune mouse HSA antiserum was used as a positive control.

Figure 5:
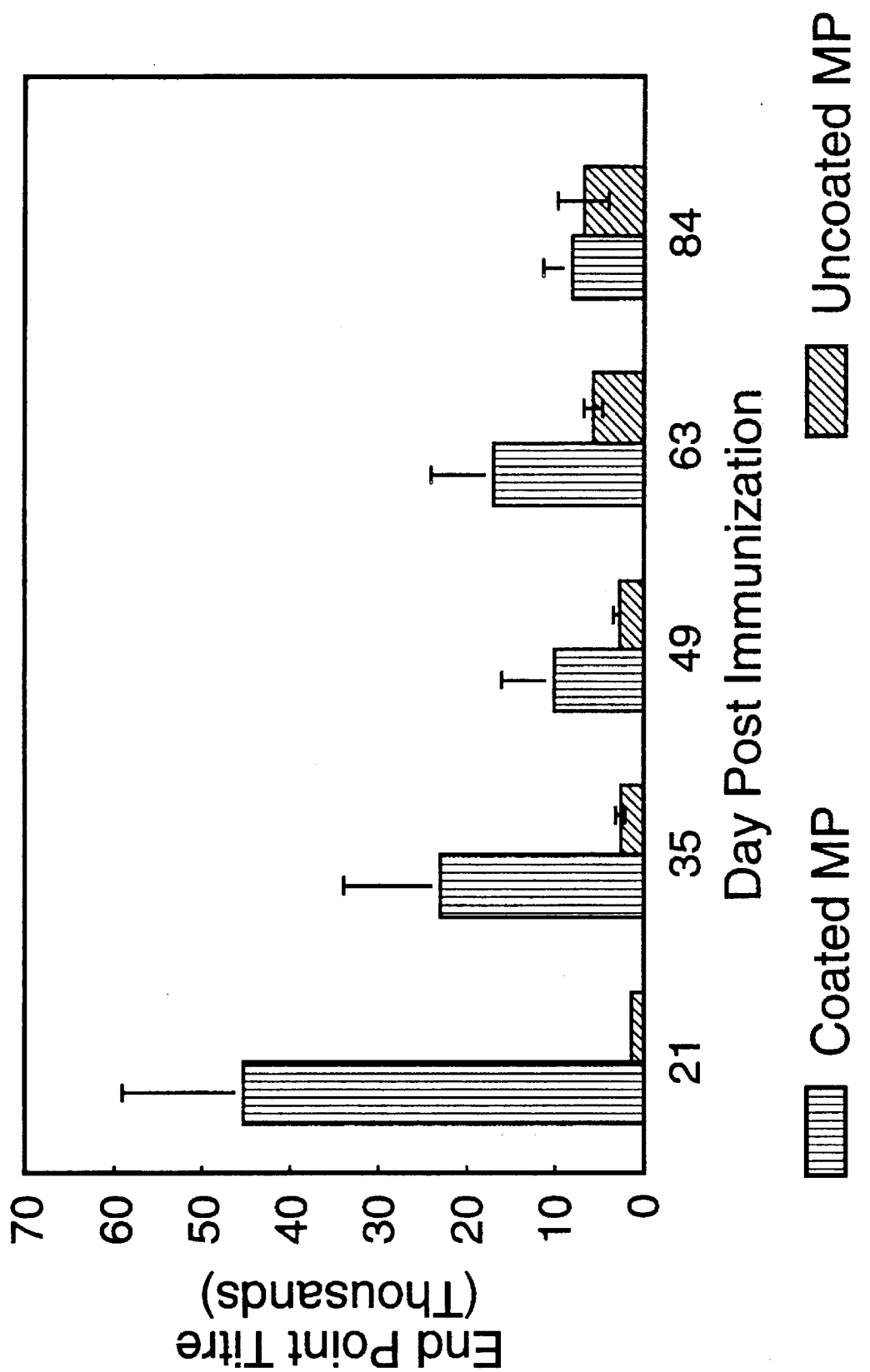
FIG. 5 shows the anti-HSA IgG serum antibody responses following various immunization protocols. Groups of 6 mice were immunized intraperitoneally (I.P.) on days 0, 7 and 14 with 250 μL of PBS, pH 7.4, containing 100 μg of HSA incorporated into TS-PDMS-coated or uncoated starch microparticles. Sera obtained on days 21, 35, 49, 63 and 84 were evaluated for the presence of anti-HSA IgG antibodies using an enzyme-linked immunosorbent assay (ELISA). 1 mg of coated or uncoated microparticles contains 50 μg of HSA.

The serum antibody titres following immunization are shown in FIG. 5. The results of immunizations with a convenient test antigen (HSA) indicate that antigen presented to the immune system entrapped in TS-PDMS starch microparticles is substantially more immunogenic than soluble antigen or antigen entrapped in uncoated starch microparticles.

Example 6

This Example describes the immunogenicity of HSA entrapped in starch microparticles in mice immunized by the intragastric route.

To examine the immunogenicity of HSA entrapped in starch microparticles formed in accordance with the present invention, groups of six, 6 to 8 week old female BALB/c mice, were immunized by the intragastric route (IG) with HSA-containing microparticles, prepared as described in Examples 1 (uncoated) and 2 (coated) above, (Table II) on days 0 +7 and +14:

TABLE II

| Group: | Microparticle[1] Type: | mg particle: | µg HSA: |
|---|---|---|---|
| A | TS-PDMS coated | 15 | 750 |
| B | TS-PDMS coated | 10 | 500 |
| C | TS-PDMS coated | 3 | 150 |
| D | TS-PDMS coated | 1.5 | 75 |
| E | TS-PDMS coated | 1 | 50 |
| F | uncoated | 15 | 750 |
| G | uncoated | 10 | 500 |
| H | uncoated | 3 | 150 |
| I | uncoated | 1.5 | 75 |
| J | uncoated | 1 | 50 |
| K | none | 0 | 0 |
| N | none | — | — |
| O | none | — | 750 |
| P | none | — | 500 |
| Q | none | — | 150 |
| R | none | — | 75 |
| S | none | — | 50 |

[1]mg of TS-PDMS coated microparticle contains 50 µg of HSA.

Sera were examined for the presence of HSA-specific antibodies on days +21, +35 and +49.

Sera and intestinal washes were examined for the presence of HSA-specific antibodies. To detect and quantify anti-HSA sIgA in the intestinal lumen, mice were sacrificed by cervical dislocation, their small intestines removed and examined for the presence of antigen-specific antibodies. Individual small intestines were detached from the pyloric sphincter to the caecum and everted over capillary tubes. The everted intestines were incubated in 5 mL of ice cold enzyme inhibitor solution (0.15M NaCl, 0.01M $Na_2HPO_4$, 0.005M EDTA, 0.002M PMSF, 0.05 U/mL Aprotinin, and 0.02% v/v $NaN_3$) for 4 hours. Intestines were removed and the supernatants clarified by centrifugation (1000 xg, 20 minutes) and stored at 0° C. until assayed. Anti-HSA sIgA titres in samples were determined by HSA-specific ELISA as described above but a goat anti-mouse IgA antiserum was used in place of the goat anti-mouse IgG antiserum.

Figure 6:
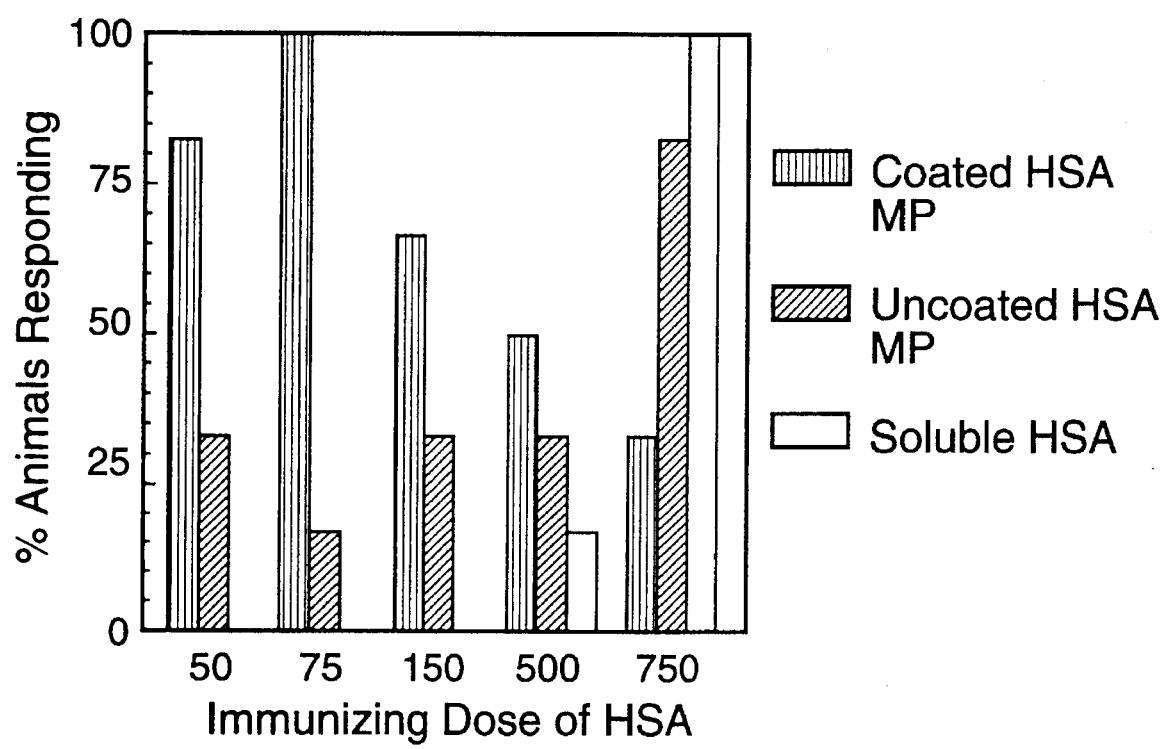
FIG. 6 shows the percentage of animals developing an anti-HSA IgG serum antibody response following intragastric immunization with HSA incorporated into uncoated or TS-PDMS coated microparticles.

The percentage of mice immunologically responding to the intragastric immunization is shown in FIG. 6. These results show that a much higher proportion of animals immunologically respond to the test antigen (HSA) when delivered using PDMS-coated microparticles compared to uncoated microparticles at physiologically relevant doses, for example, 75 µg or less.

Figure 7:
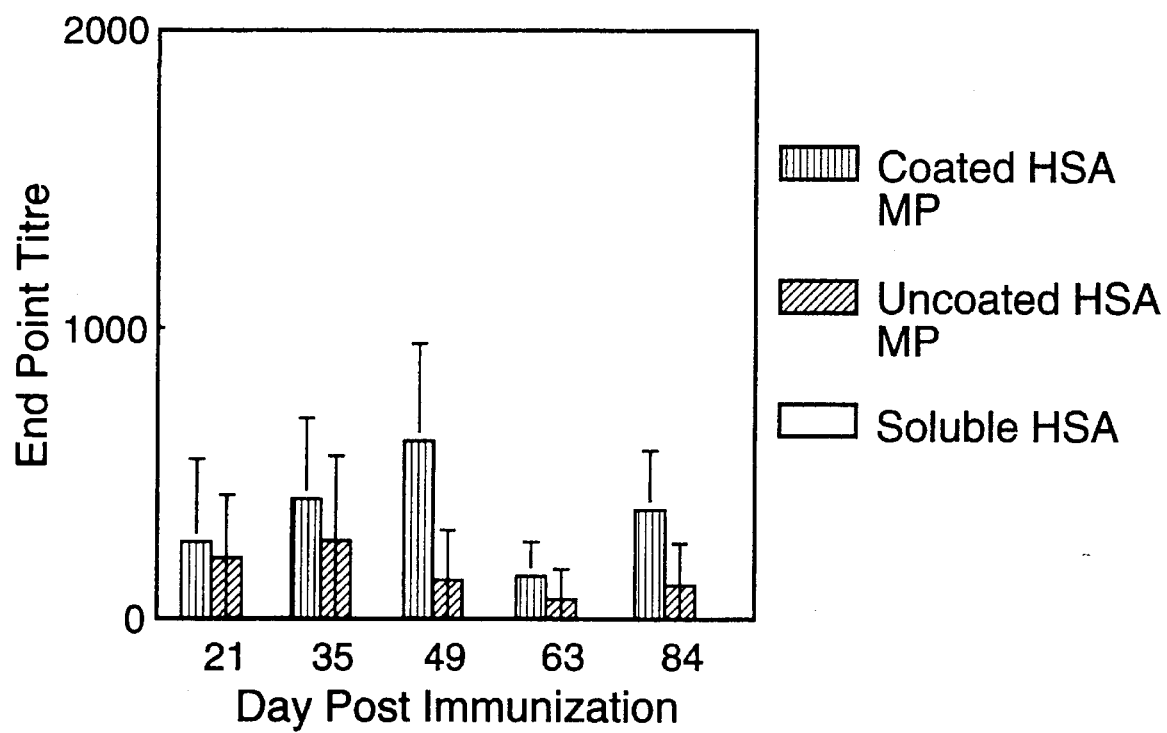
FIG. 7 shows the anti-HSA IgG serum antibody titres in six mice immunized intragastrically with a 50 μg dose of uncoated or TS-PDMS coated microparticles. Animals were immunized on days 0, 7 and 14 with 0.5 mL of 0.2M NaHCO₃ containing 50 μg of HSA incorporated into TS-PDMS-coated or uncoated starch microparticles or soluble HSA. Sera obtained on days 21, 35, 49, 63 and 84 were evaluated for the presence of anti-HSA IgG antibodies using an ELISA. 1 mg of coated or uncoated microparticles contains 50 μg of HSA.
Figure 8:
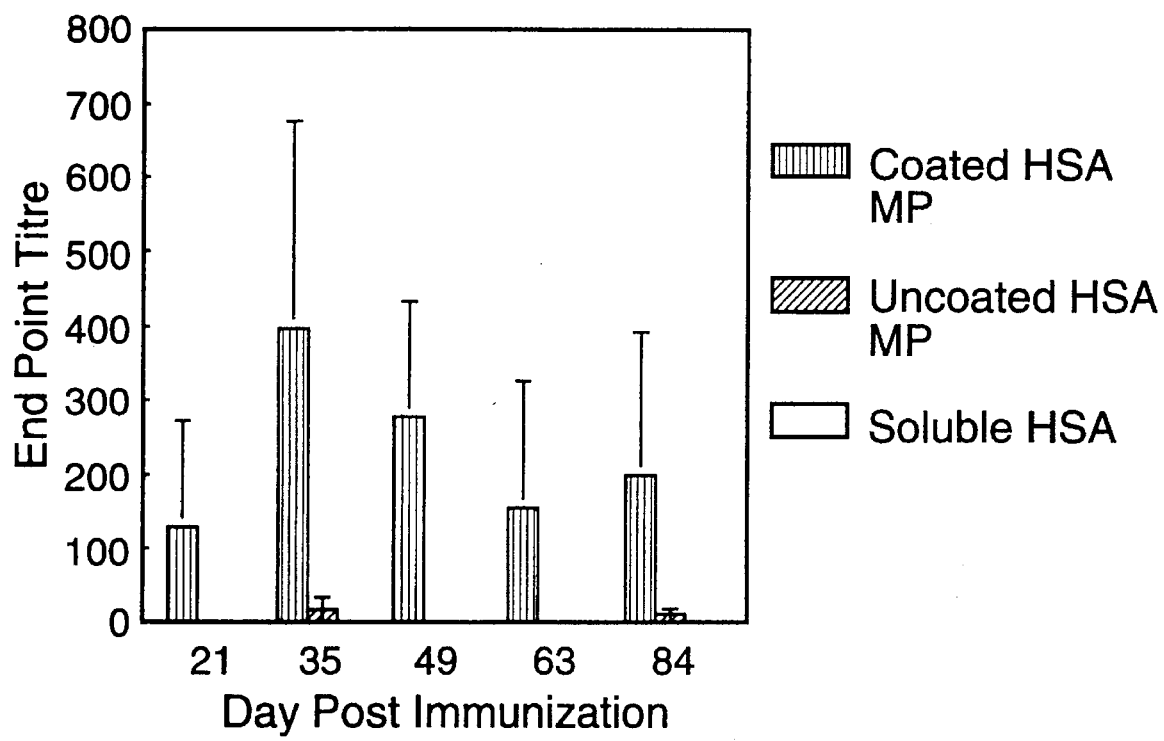
FIG. 8 shows the anti-HSA IgG serum antibody titres in six mice immunized intragastrically with a 75 μg dose of uncoated or TS-PDMS coated microparticles. Animals were immunized on days 0, 7 and 14 with 0.5 mL of 0.2M NaHCO$_3$ containing 75 μg of HSA incorporated into TS-PDMS-coated or uncoated starch microparticles or soluble HSA. Sera obtained on days 21, 35, 49, 63 and 84 were evaluated for the presence of anti-HSA IgG antibodies using an ELISA. 1 mg of coated or uncoated microparticles contains 50 μg of HSA.

The serum IgG HSA-specific antibody titres following IG immunization are shown in FIGS. 7 (50 µg of HSA) and 8 (75 µg of HSA). These results indicate that a test antigen (HSA) incorporated into PDMS-coated microparticles is substantially more immunogenic than antigen incorporated into uncoated particles when delivered by the intragastric route.

Example 7

This Example describes the immunogenicity of herpes simplex type 2 virus (HSV-2) antigens entrapped in microparticles in mice immunized by the intraperitoneal and intragastric routes.

To examine the stimulation of virus-specific immune responses by viral antigens entrapped in microparticles, mice were immunized IP and IG with HSV-2 infected cell lysates entrapped within TS-PDMS coated microparticles containing HSA as a carrier protein. Groups of 5, 6–8 week old female BALB/c mice were immunized by the intraperitoneal (IP) and intragastric (IG) routes with the following materials on days 0, +7 and +14:

1. 125 µg of HSV-2 infected cell lysate protein in 250 µL of PBS (IP) or 500 µL of $NaHCO_3$ (IG).
2. 16 mg of TS-PDMS coated microparticles containing about 125 µg of HSV-2 infected cell lysate.
3. 8 mg of TS-PDMS coated microparticles containing about 63 µg of HSV-2 infected cell lysate protein.

Sera were examined for the presence of HSV-2 specific IgG antibodies and demonstrated that viral proteins may be entrapped within TS-PDMS coated starch microparticles without reduction in immunogenicity.

Example 8

This Example describes the immunogenicity of whole influenza virus entrapped in microparticles in mice immunized IP.

To examine the immunogenicity of Flu X31/HSA TS-PDMS coated microparticles, prepared as described in Example 2, groups of six Balb/c mice were immunized by intraperitoneal (IP) route with the following materials:

1. 5 µg of Flu X31 and 15 µg of HSA in soluble form.
2. 5 µg of Flu X31 and 15 µg of HSA mixed with TS-PDMS coated microparticles.
3. Flu X31/HSA TS-PDMS coated microparticles containing 5 µg of Flu X31 and 15 µg of HSA.

Figure 9:
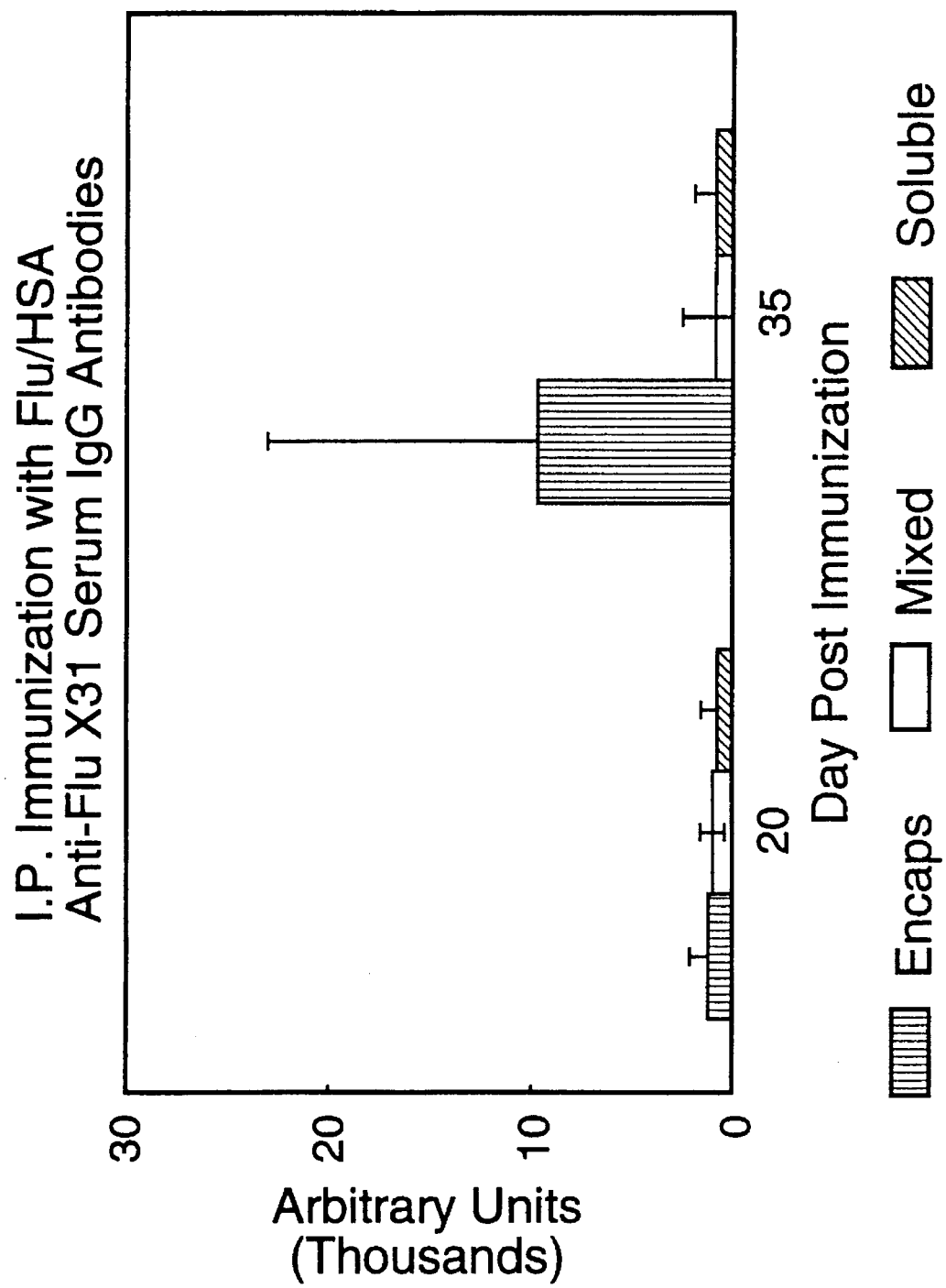
FIG. 9 shows the anti-Flu X31 (i.e. influenza virus type A strain X31) serum antibody titres in mice immunized by the intraperitoneal route with soluble Flu X31/HSA, Flu X31/HSA mixed with microparticles coated with TS-PDMS or Flu X31HSA entrapped in TS-PDMS-coated microparticles.
Figure 10:
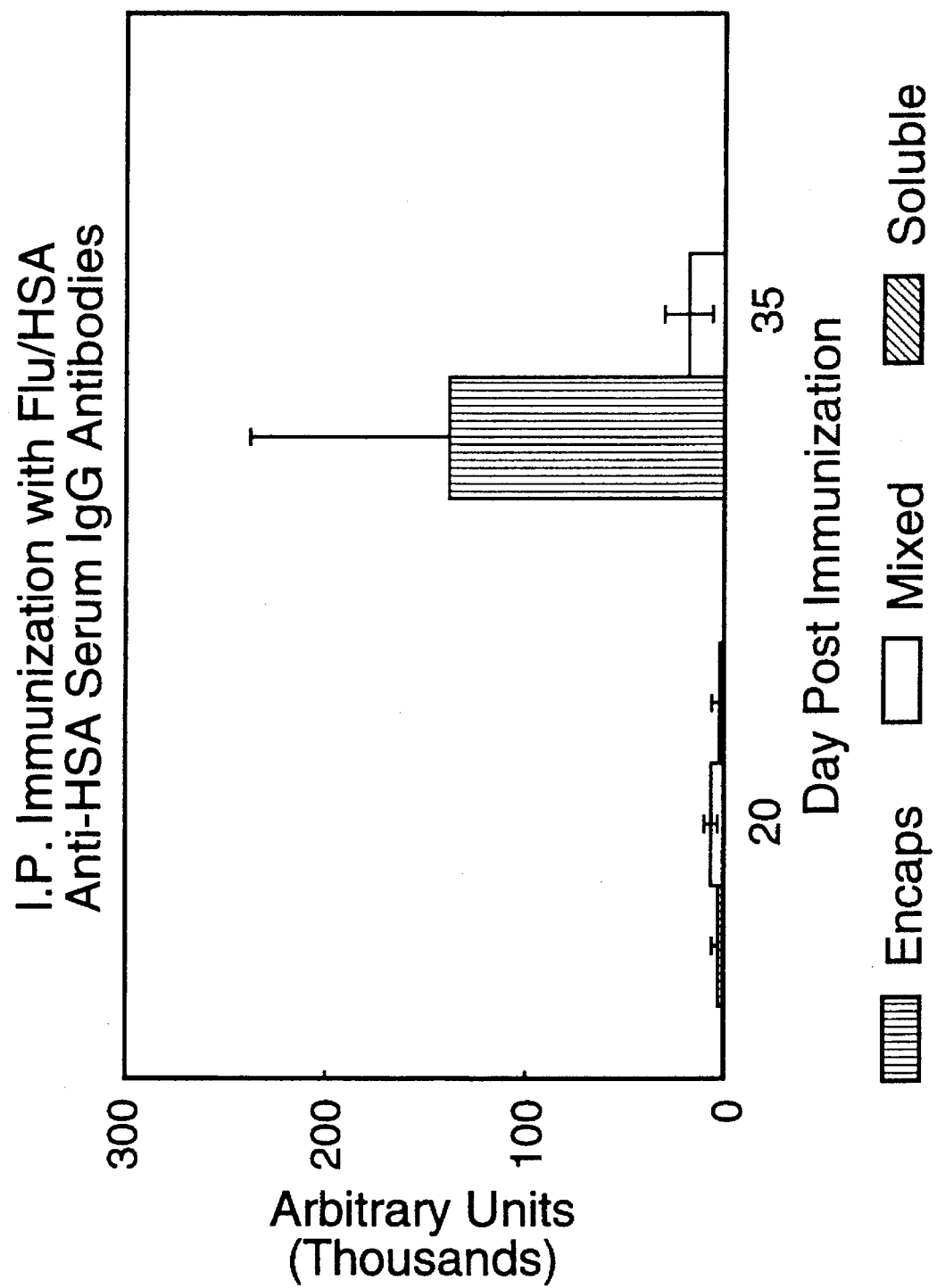
FIG. 10 shows the anti-HSA antibody titres in the sera of mice immunized by the intraperitoneal route with soluble Flu X31/HSA, Flu X31/HSA mixed with microparticles coated with TS-PDMS or Flu X31/HSA entrapped in TS-PDMS-coated microparticles.

The mice received a single immunization IP on day 0 and were bled at days +20 and +35. The sera obtained were assayed for anti-Flu X31 and anti-HSA IgG antibodies by antigen-specific ELISA. The anti-Flu X31 ELISA was performed as described above but the plates were coated overnight at 4° C. with 100 µL of whole influenza virus at 5 µg per mL in place of the HSA and an anti-Flu antibody was used as a positive control. These antibody titres are shown in FIGS. 9 and 10 for Flu X31 and HSA immunized mice respectively.

As described in Example 5 above, HSA alone or HSA mixed with TS-PDMS coated microparticles were poorly immunogenic. In contrast, HSA entrapped in TS-PDMS coated microparticles elicited high antibody titres.

Mice immunized IP with all three preparations showed similar serum IgG anti-Flu X31 antibody responses on day +20. At day +35 the IgG anti-Flu X31 antibody titre in the serum of mice immunized IP with Flu X31/HSA incorporated in TS-PDMS coated microparticles was about 10-fold greater than the titres obtained following immunization with soluble Flu X31 or Flu X31 mixed with TS-PDMS coated microparticles.

The studies presented in this Example demonstrate that viral antigens from influenza virus can be made more immunogenic and elicit high levels of serum IgG antibodies, when the antigens are entrapped in microparticles formed in accordance with the present invention.

Example 9

This Example describes the immunogenicity of whole influenza virus entrapped in microparticles in mice immunized IN.

To examine the immunogenicity of Flu X31/HSA TS-PDMS coated microparticles, prepared as described in Example 2, groups of six Balb/c mice were immunized by the intranasal (IN) route with the following materials:

1. 10 µg of Flu X31 and 30 µg of HSA in soluble form.
2. Flu X31/HSA TS-PDMS coated microparticles containing 10 µg of Flu X31 and 30 µg of HSA.

Figure 11:
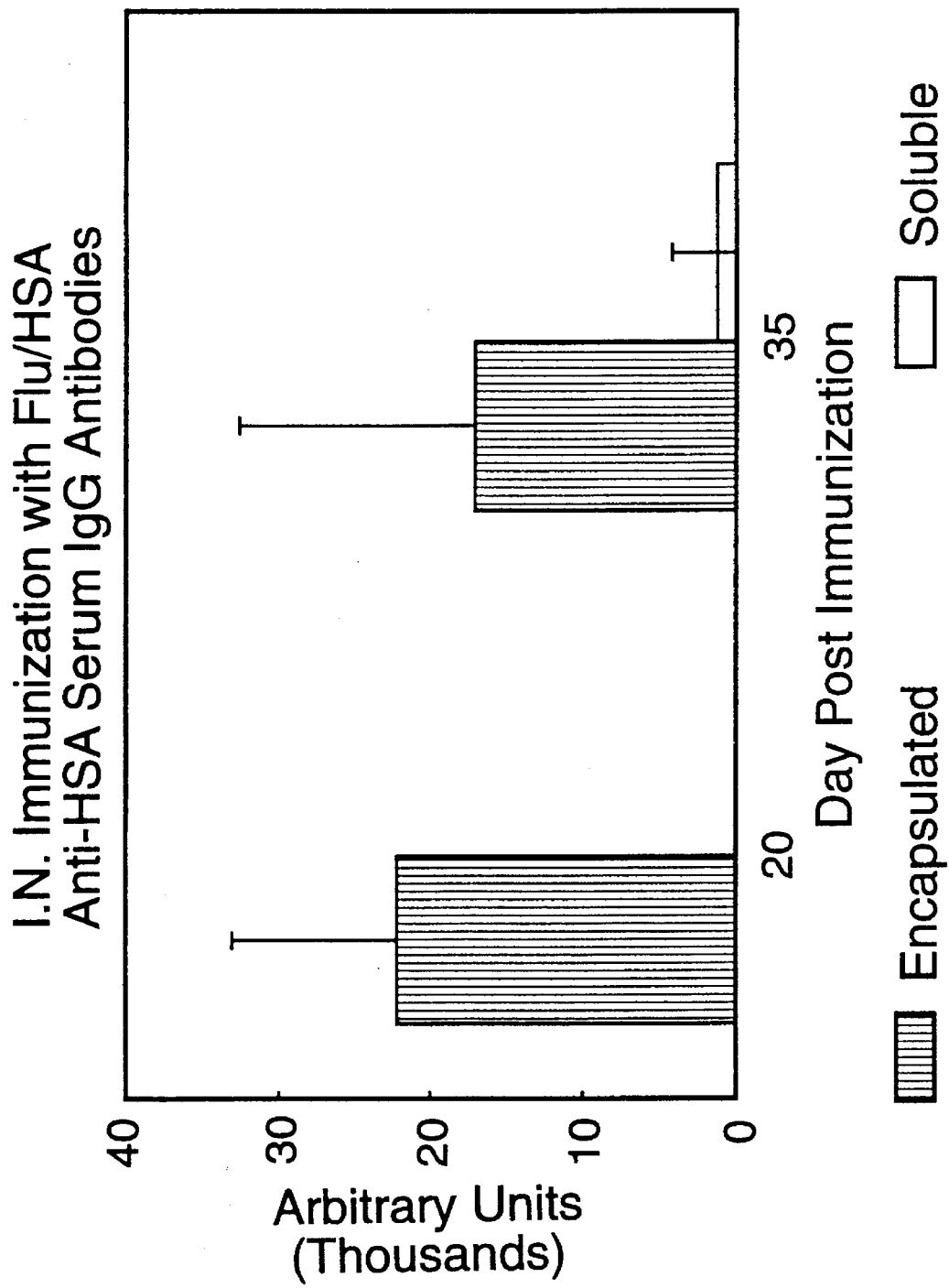
FIG. 11 shows the anti-Flu X31 antibody titres in the sera of mice immunized by the intranasal route with soluble Flu X31/HSA or Flu X31/HSA entrapped in TS-PDMS-coated microparticles.

Mice were immunized IN on days 0 +7 and +14 and bled on days +20 and +35. The sera obtained were assayed for anti-Flu X31 and anti-HSA IgG antibodies by antigen-specific ELISA as described above. These serum antibody titres are shown in FIGS. 11 and 12 for HSA and Flu X31 respectively.

Mice immunized IN with soluble antigen had undetectable levels of HSA-specific serum IgG antibodies. Mice immunized with Flu X31/HSA TS-PDMS coated microparticles showed a serum anti-HSA antibody response.

Figure 12:
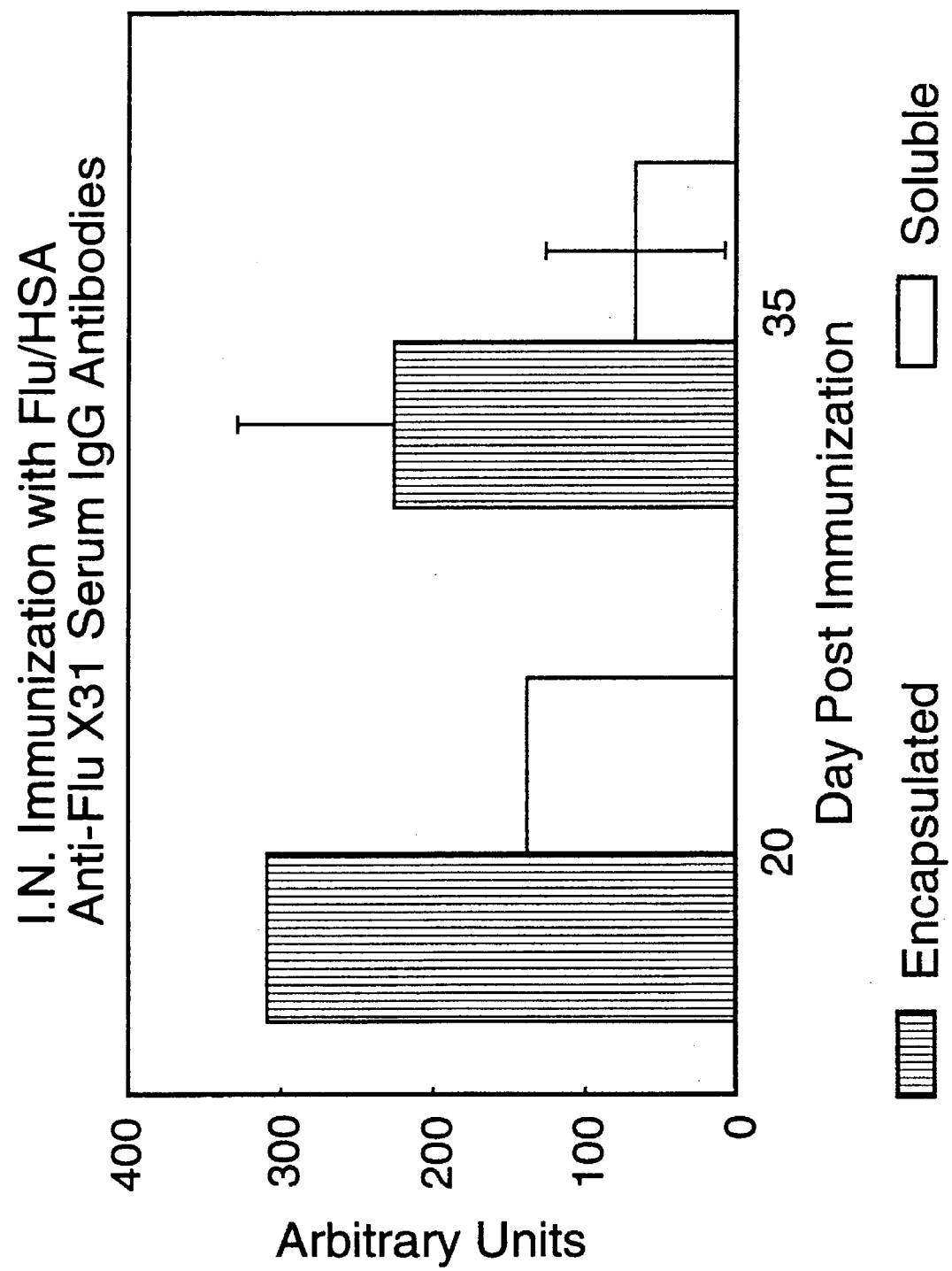
FIG. 12 shows the anti-HSA antibody titres in the sera of mice immunized by the intranasal route with soluble Flu X31/HSA or Flu X31/HSA entrapped in TS-PDMS-coated microparticles.

The anti-Flu X31 antibody titres in mice immunized IN are shown in FIG. 12 and show that the highest titres were obtained following immunization with Flu X31/HSA TS-PDMS coated microparticles.

The results of the IN immunizations described in this Example show that the immunogenicity of an antigen (HSA) and a mixture of influenza virus antigens can be enhanced by entrapment in microparticles formed in accordance with the present invention. In particular, the normally non-immunogenic antigen HSA following incorporation into microparticles was made immunogenic.

SUMMARY OF THE DISCLOSURE

In summary of this disclosure, the present invention provides a particulate carrier for an agent, particularly one having biological activity, comprising a core of polysaccharide and proteinaceous material and an organometallic polymer bonded to the core. The particulate carriers in the form of microparticles are able to efficiently deliver agents to the cells of the immune system of a subject following mucosal or parenteral administration to produce an immune response. Modifications are possible within the scope of this invention.

What we claim is:

1. A particulate carrier, which comprises:

a solid matrix comprising a polysaccharide and a proteinaceous material, and a functionalized silicone polymer bonded to the matrix.

2. The particulate carrier of claim 1 wherein the polysaccharide is selected from the group consisting of dextran, starch, cellulose, derivatives and mixtures thereof.

3. The particulate carrier of claim 1 wherein the polysaccharide is a soluble starch.

4. The particulate carrier of claim 2 wherein the proteinaceous material is a material having immunogenic biological activity.

5. The particulate carrier of claim 1 wherein said matrix contains an additional material having biological activity.

6. The particulate carrier of claim 5 wherein the additional material having biological activity is selected from the group consisting of proteins, peptides, antigens, bacteria, bacterial lysates, viruses, virus-infected cell lysates, antibodies, carbohydrates, nucleic acids, lipids, glycolipids haptens, pharmacologically-active materials, and combinations, derivatives and mixtures thereof.

7. The particulate carrier of claim 4 or 5 wherein the material having biological activity is immunogenic.

8. The particulate carrier of claim 4 or 5 wherein the material having biological activity comprises human serum albumin, herpes simplex virus type 2— infected cell lysate, an influenza virus, or an influenza viral protein.

9. The particulate carrier of claim 1 wherein the functionalized silicone comprises an end-substituted silicone.

10. The particulate carrier of claim 9 wherein the end-substituted silicone is (trialkoxysilyl)alkyl-terminated polydialkylsiloxane.

11. The particulate carrier of claim 10 wherein the end-substituted silicone is 3-(triethoxysilyl)propyl-terminated polydimethylsiloxane.

12. The particulate carrier of claim 11 wherein said silicone has a molecular weight of from about 400 to about 1,000,000 Daltons.

13. A particulate carrier, which comprises:

a solid matrix having a particle size of about 10 nm to about 50 µm comprising a polysaccharide and up to about 33 wt % of a proteinaceous material, and a functionalized polysiloxane having a molecular weight of from about 400 to about 1,000,000 Daltons in an amount of about 0.5 to about 5 wt % of the matrix and bonded to the matrix.

14. The particulate carrier of claim 13 wherein said proteinaceous material comprises from about 0.5 to about 10 wt % of said matrix.

15. The particulate carrier of claim 13 wherein said matrix further comprises about 0.5 to about 30 wt % of an additional biologically-active material.

16. The particulate carrier of claim 15 wherein said biologically-active material comprises about 0.5 to about 5.0 wt %.

17. The particulate carrier of claim 13, wherein said polysiloxane has a molecular weight of from about 700 to about 60,000 Daltons.

18. The particulate carrier of claim 13 which has a particle size of about 1 to about 10 µm.

19. A method for producing a particulate carrier, which comprises:

(a) forming an aqueous composition comprising a dissolved polysaccharide and a dispersed or dissolved proteinaceous material by dissolving said polysaccharide in a polar solvent therefor to form a solution thereof, dissolving or dispersing said proteinaceous material in an aqueous solvent therefor to form a solution or dispersion thereof, and mixing the resulting media;

(b) forming an emulsion in which the aqueous composition is the dispersed phase by dispersing said aqueous composition in a water-immiscible fluid capable of forming a water-in-oil (c) forming from said emulsion a particulate carrier comprising a matrix of said polysaccharide and proteinaceous material having bonded thereto a functionalized silicone polymer, by adding said water-in-oil emulsion dropwise to a solvent for water and said water-immiscible fluid, said solvent containing a functionalized silicone; and (d) collecting the particulate carrier so formed.

20. The method of claim 19 wherein said polysaccharide is starch and said solvent for said starch is dimethylsulfoxide.

21. The method of claim 19 wherein said water-immiscible fluid comprises a vegetable oil.

22. The method of claim 19 wherein said oil-in-water emulsion also contains a surfactant.

23. The method of claim 19 wherein said functionalized silicone, comprises an end-substituted silicone.

24. The method of claim 19 wherein said solvent for water comprises a ketone.

25. The method of claim 24 wherein said ketone is acetone.

26. The method of claim 19 which is carried out under conditions which are not conducive to denaturation of said proteinaceous material.

27. An immunogenic composition formulated for mucosal or parenteral administration, comprising a particulate carrier of claim 1 having biological activity and a physiological acceptable carrier therefor.

28. A method of producing an immune response in a subject, comprising administering to the subject an effective amount of the immunogenic composition of claim 27.

29. The method of claim 28 wherein the composition is administered by mucosal or parenteral administration.

30. The method of claim 29 wherein the immune response is an antibody response.

* * * * *